United States Patent
Nawata et al.

(10) Patent No.: US 7,682,428 B2
(45) Date of Patent: Mar. 23, 2010

(54) OXYGEN CONCENTRATION APPARATUS

(75) Inventors: Hideo Nawata, Hino (JP); Naotoshi Fujimoto, Hino (JP); Kanji Kurome, Hino (JP); Sadakazu Matsubara, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 901 days.

(21) Appl. No.: 10/569,463

(22) PCT Filed: Aug. 26, 2004

(86) PCT No.: PCT/JP2004/012694

§ 371 (c)(1),
(2), (4) Date: Feb. 24, 2006

(87) PCT Pub. No.: WO2005/018789

PCT Pub. Date: Mar. 3, 2005

(65) Prior Publication Data

US 2007/0039466 A1 Feb. 22, 2007

(30) Foreign Application Priority Data

Aug. 26, 2003 (JP) ............... 2003-301021
Sep. 2, 2003 (JP) ............... 2003-309861

(51) Int. Cl.
*B01D 53/02* (2006.01)
(52) U.S. Cl. ............... 96/113; 96/130; 96/143; 128/205.12; 128/205.27
(58) Field of Classification Search ............ 95/96, 95/130, 148; 96/113, 114, 115, 121, 130; 128/205.12, 205.27
See application file for complete search history.

(56) References Cited

U.S. PATENT DOCUMENTS 4,822,384 A * 4/1989 Kato et al. ............... 96/110

(Continued)

FOREIGN PATENT DOCUMENTS

JP 61-131756 A 6/1986

(Continued)

OTHER PUBLICATIONS

International Search Report, Feb. 2005.

(Continued)

*Primary Examiner*—Robert A Hopkins
(74) *Attorney, Agent, or Firm*—Rader, Fishman & Grauer, PLLC

(57) ABSTRACT

An oxygen concentration apparatus (300) according to the present invention has: pressure swing adsorption type oxygen concentration means (310); and a control means (350) that controls switching means (316) that switches between intake of pressurized air into an adsorption column (312) and exhaust from the adsorption column. The switching means is controlled based on pressure in oxygen concentrated gas in the conduit measured by pressure measuring means to adjust a cycle of adsorption and regeneration processes of the oxygen concentration means so that pressure at the upstream of flow rate adjusting means (340) can be controlled and, as a result, the need for a mechanical pressure regulating valve, that has been needed conventionally, can be eliminated. Further, there is also shown a gas supply apparatus that comprises ultrasonic type gas concentration and flow rate measuring means that comprises, in turn, two ultrasonic transducers that is disposed in an opposed manner in the conduit through which product gas flows so that a concentration value measured when the product gas output is stopped is determined to be a product gas concentration.

17 Claims, 9 Drawing Sheets

U.S. PATENT DOCUMENTS

| | | | |
|---|---|---|---|
| 5,746,806 A | 5/1998 | Aylsworth et al. | |
| 7,273,051 B2 * | 9/2007 | Whitley et al. | 128/205.11 |

FOREIGN PATENT DOCUMENTS

| | | | |
|---|---|---|---|
| JP | 02-157011 A | 6/1990 | |
| JP | 03-022185 A | 1/1991 | |
| JP | 03-22185 B2 | 3/1991 | |
| JP | 03-27254 U | 3/1991 | |
| JP | 07-136272 A | 5/1995 | |
| JP | 3033038 U | 1/1997 | |
| JP | 09-187509 A | 7/1997 | |
| JP | 09-192222 A | 7/1997 | |
| JP | 09-276640 A | 10/1997 | |
| JP | 2000-352482 A | 12/2000 | |
| JP | 2001-505078 A | 4/2001 | |
| JP | 2001-187145 A | 7/2001 | |
| JP | 2002-045424 A | 2/2002 | |
| JP | 2002-085567 A | 3/2002 | |
| JP | 2002-121010 A | 4/2002 | |
| JP | 2002-214012 A | 7/2002 | |
| JP | 2002-253675 A | 9/2002 | |
| JP | 2002-306603 A | 10/2002 | |
| JP | 2003-135601 A | 5/2003 | |
| JP | 2003-137510 A | 5/2003 | |
| JP | 2003-144549 A | 5/2003 | |
| JP | 2003-144550 A | 5/2003 | |
| TW | 492884 | 7/2002 | |
| WO | WO-82/01815 A1 | 6/1982 | |
| WO | WO-01/72364 A1 | 10/2001 | |
| WO | WO-02/057770 A1 | 7/2002 | |

OTHER PUBLICATIONS

Office Action of Patent Application No. 09820210430 issued on Apr. 13, 2009 (Taiwan).

Office Action of Patent Application No. 2003-309861 mailed on Mar. 3, 2009 (Japan).

Office Action of Patent Application No. 2003-301021 mailed on Mar. 24, 2009 (Japan).

* cited by examiner

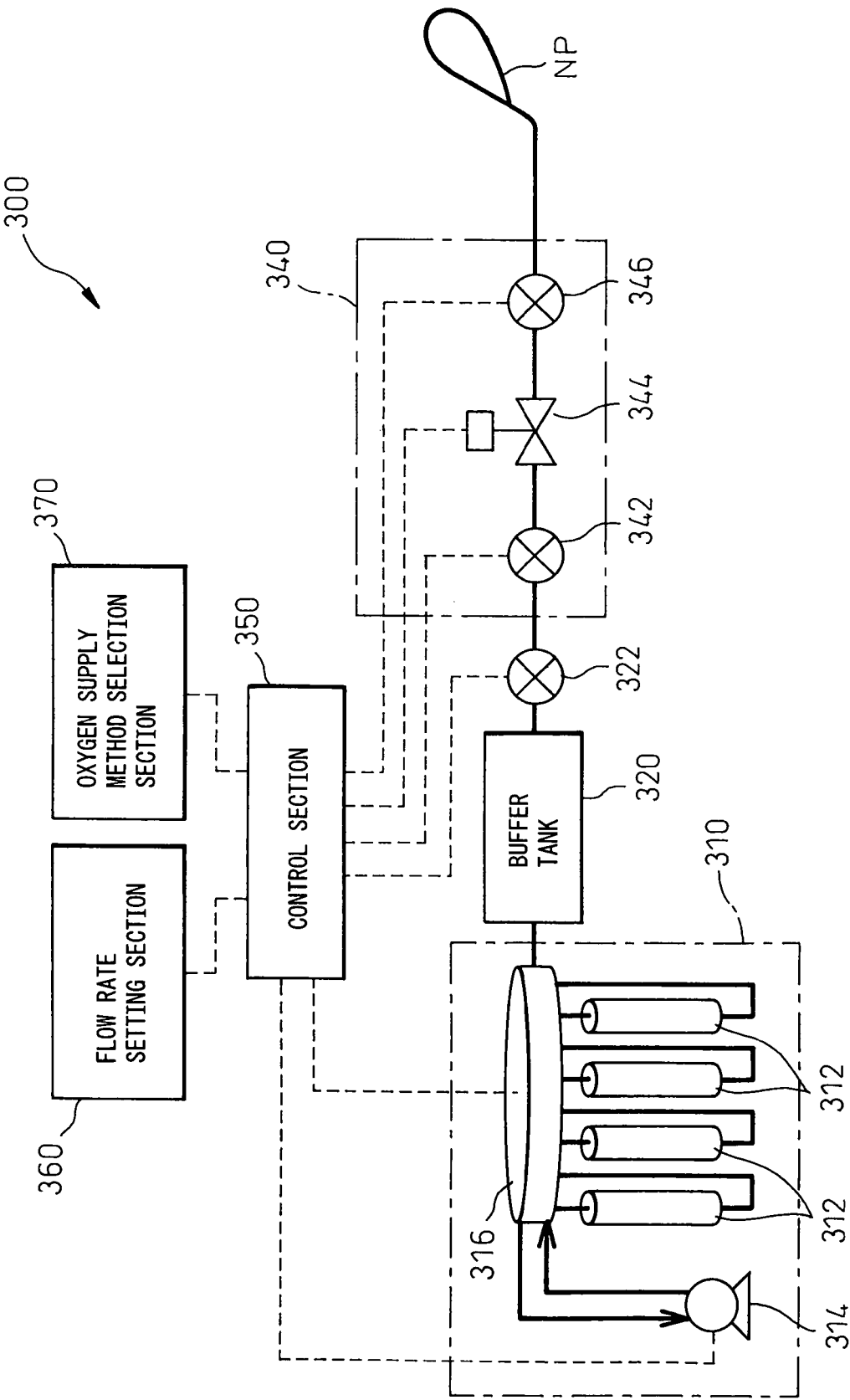

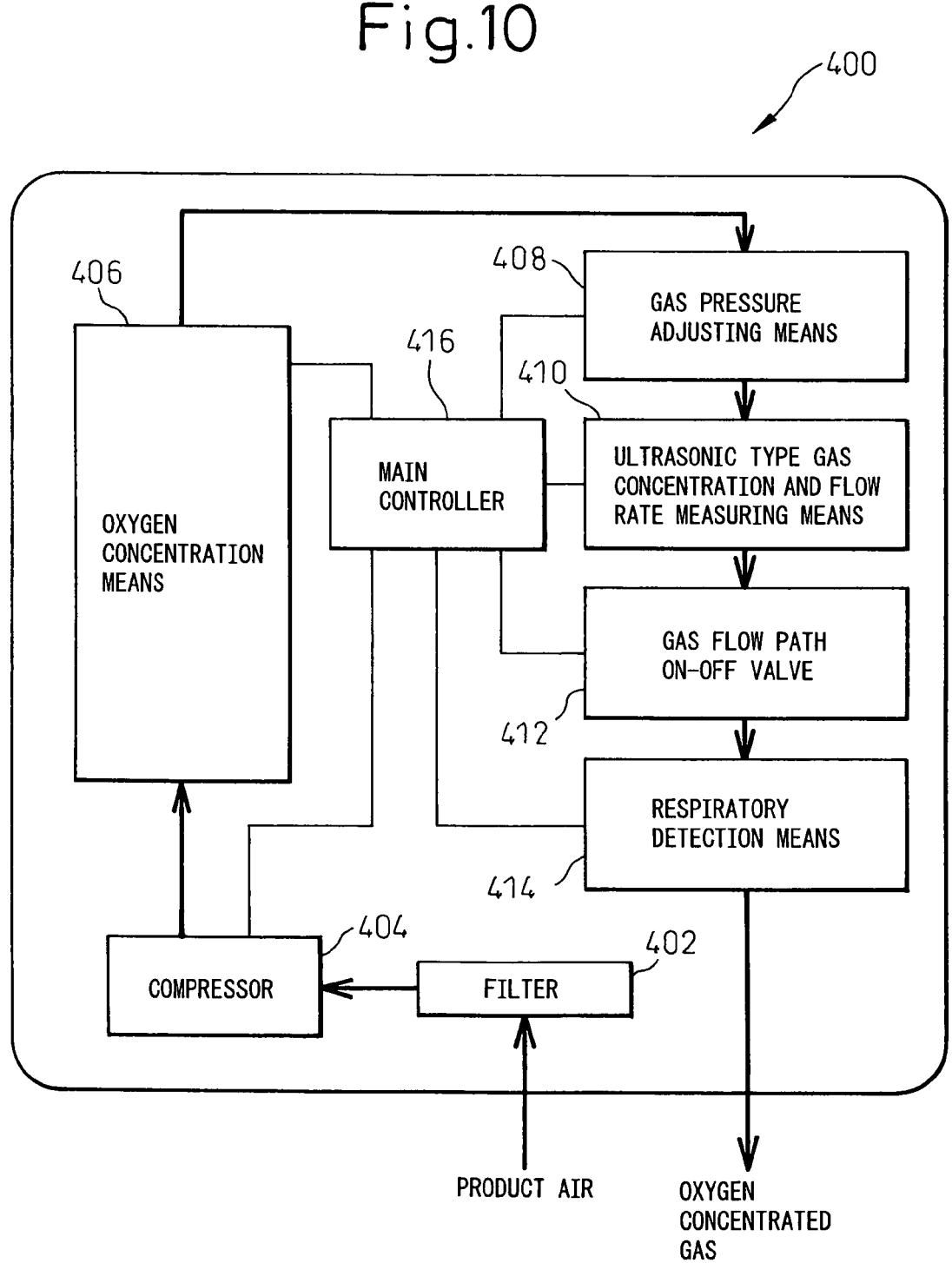

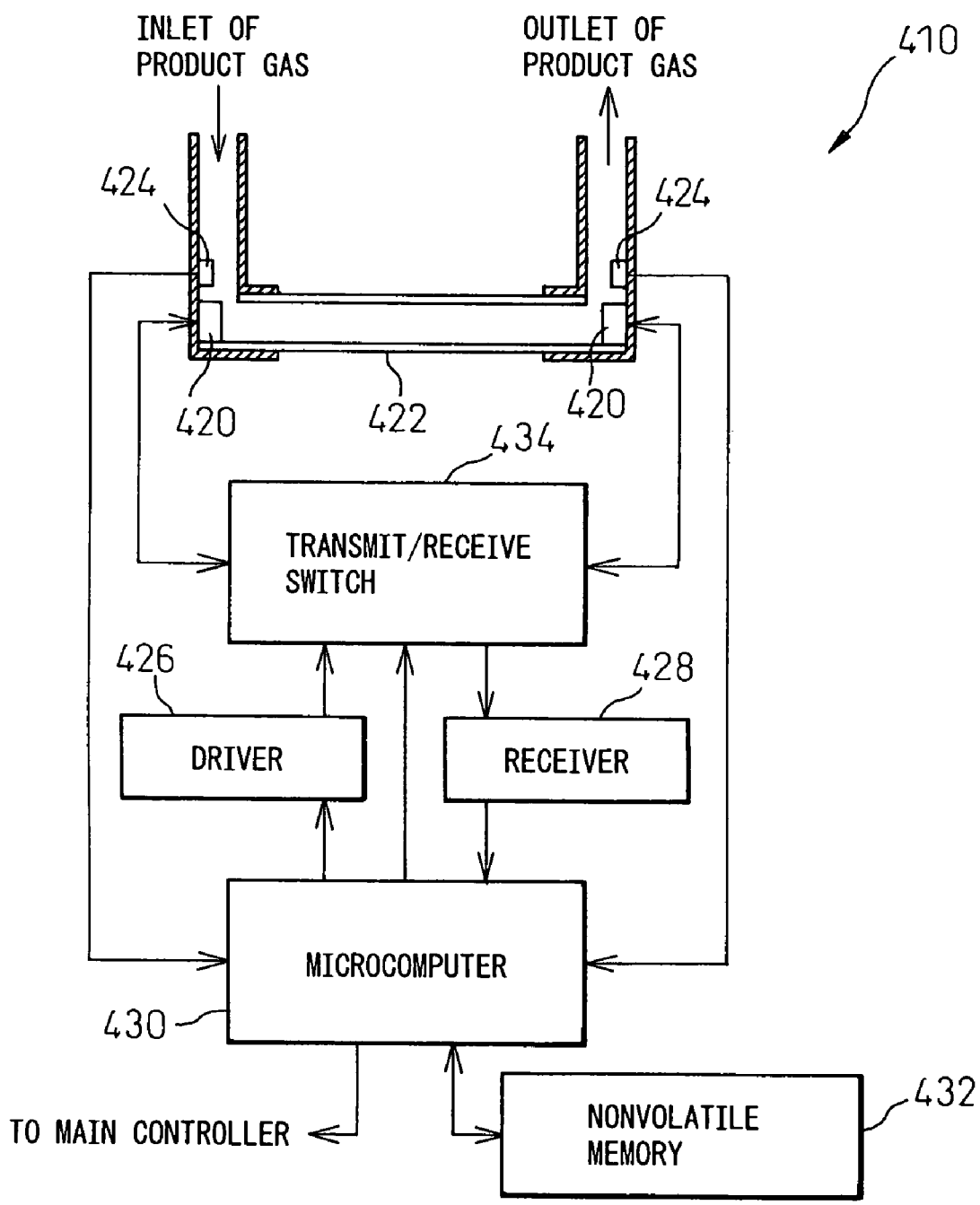

OXYGEN CONCENTRATION APPARATUS

BACKGROUND OF THE INVENTION

1. Field of the Invention

The present invention relates to a pressure swing adsorption-type oxygen concentration apparatus using an adsorbent that preferentially adsorbs nitrogen rather than oxygen and, in particular, it relates to a medical oxygen-concentration apparatus used in oxygen-inhalation therapy that is a treatment for respiratory diseases.

2. Description of the Related Art

In recent years, the number of patients that suffer from respiratory diseases such as asthma, pulmonary emphysema, chronic bronchitis and the like has been growing. One of the most effective therapy methods for such respiratory diseases is oxygen inhalation therapy that allows the patient to inhale an oxygen-concentrated gas or oxygen-enriched air. As a source of the oxygen-concentrated gas or the oxygen-enriched air supplied to the patient (referred to as the "oxygen supply source" in this specification), an oxygen concentration apparatus, liquid oxygen, an oxygen concentrated gas tank and the like are well-known but, among others, in view of convenience in use and ease of maintenance and management, the oxygen concentration apparatus is mainly used in home oxygen therapy.

Though a membrane type oxygen concentration apparatus that uses a membrane for selectively permeating oxygen is known, a pressure swing adsorption type oxygen concentration apparatus that uses an adsorbent that preferentially adsorbs nitrogen, and that can provide higher concentration of oxygen, is more widely used.

Known methods for supplying the oxygen concentrated gas generated in the oxygen concentration apparatus include: a method for supplying the oxygen concentrated gas at a constant flow rate continuously; and a method for supplying the oxygen concentrated gas only in an inspiratory phase, or in a portion of the inspiratory phase, in synchronization with the patient's respiration.

When the oxygen concentrated gas at a constant flow rate is supplied continuously, the oxygen concentration apparatus is provided with a flow rate adjuster for supplying the oxygen concentrated gas at a prescribed constant flow rate to the patient. This flow rate adjuster may be an orifice type flow rate adjuster, a flow rate adjuster using a needle valve, and a feedback type flow rate adjuster using a flow rate sensor. The orifice type flow rate adjuster has a plurality of orifices of different diameters so that one of the plurality of orifices can be selected to obtain a desired flow rate under the pressure condition at the upstream of the orifice. The feedback type flow rate adjuster controls a degree of opening of a throttle valve based on a measurement value by the flow rate sensor.

Further, Japanese Unexamined Patent Publication No. S61-131756 and Japanese Examined Patent Publication No. H03-22185 disclose an oxygen supply method for supplying oxygen concentrated gas only in an inspiratory phase, or in a portion of the inspiratory phase, in synchronization with the patient's respiration, and a pressure swing adsorption type oxygen concentration apparatus with this respiratory synchronous oxygen supplying method.

Still further, Japanese Unexamined Patent Publication No. 2001-187145, Japanese Unexamined Patent Publication No. 2003-144549, and Japanese Unexamined Patent Publication No. 2003-144550 disclose a mechanical pressure regulating valve having a piston and a spring used in the oxygen supply method in a continuous or respiratory synchronous intermittent manner described above.

Still further, Japanese Unexamined Patent Publication No. 2000-352482, Japanese Unexamined Patent Publication No. 2002-121010, Japanese Unexamined Patent Publication No. H07-136272, and Japanese Unexamined Patent Publication No. 2002-45424 disclose a battery-driven mobile or portable oxygen concentration apparatus that extends the area of activity of the patient and contributes to an improved quality of life (QOL).

On the other hand, when the oxygen concentration apparatus supplies the oxygen concentrated gas to the patient, the oxygen concentration of the oxygen concentrated gas may reduce due to degradation of the adsorbent, failure of the concentration apparatus itself and so on. The patient cannot obtain a sufficient therapeutic effect with reduced oxygen concentration of the oxygen concentrated gas and, therefore, it is desirable to provide the oxygen concentration apparatus with an oxygen concentration sensor for measuring the concentration of the oxygen concentrated gas.

While a zirconia type oxygen concentration sensor has been typically used as the oxygen concentration sensor for measuring the oxygen concentration of the oxygen concentrated gas, Japanese Unexamined Patent Publication No. 2002-214012 and Japanese Unexamined Patent Publication No. 2003-135601 disclose an ultrasonic type gas concentration and flow rate measuring apparatus.

Hereinafter, a principle of gas concentration measurement by the ultrasonic type gas concentration and flow rate measuring means will be described.

Two ultrasonic transducers that can transmit and receive ultrasonic waves with each other are disposed in an opposed manner in a line through which a product gas flows so that the ultrasonic waves can be transmitted and received in the forward direction of the gas flow. Assuming that a sound velocity observed in this case is $V_1$, a sound velocity in immobile gas is C and a flow velocity of the gas in the line is V, $V_1$ can be expressed by the following formula (1):

$$V_1 = C + V \tag{1}$$

Then, a sound velocity $V_2$ observed when the ultrasonic waves are transmitted and received in the reverse direction of the gas flow can be expressed by the following formula (2):

$$V_2 = C - V \tag{2}$$

Therefore, even if the flow velocity V of the gas is unknown, the flow velocity V of the gas can be canceled by adding the formulas (1) and (2) and, as a result, only the sound velocity C in the immobile gas can be calculated by the following formula (3):

$$C = (V_1 + V_2)/2 \tag{3}$$

Further, assuming that a gas temperature is T, a ratio of specific heat of the gas is k, a gas constant is R and an average molecular weight of the gas is M, it is known that the sound velocity C in the immobile gas can be expressed by the following formula (4):

$$C = \sqrt{\frac{kRT}{M}} \tag{4}$$

In the formula (4), k and R are constant and the value of C can be obtained by the formula (3) and, therefore, if only the gas temperature T is measured, the formula (4) can be transformed into the formula (5) to obtain the average molecular weight M of the gas:

$$M = kRT/C^2 \tag{5}$$

Thus, for example, if the measured gas is a two-component gas consisting of oxygen and nitrogen, assuming that the oxygen concentration is x, the nitrogen concentration is 1−x, a molecular weight of the oxygen is 32 and a molecular weight of the nitrogen is 28, the oxygen concentration x can be determined by using the relationship of the following formula (6):

$$32x+28(1-x)=M \tag{6}$$

Further, a principle of flow rate measurement in the ultrasonic type gas concentration flow rate measuring apparatus in which two ultrasonic transducers are arranged in an opposed manner is as follows.

By using the formulas (1) and (2) described above, even if the sound velocity C in the immobile gas is unknown, the flow velocity V of the gas can be obtained by the following formula (7):

$$V=(V_1-V_2)/2 \tag{7}$$

Then, if the flow velocity V of the gas can be obtained, the flow rate of the gas can be obtained easily by multiplying it by a cross sectional area of the line through which the gas flows.

SUMMARY OF THE INVENTION

In an oxygen concentration apparatus used in oxygen inhalation therapy, in particular, in a portable oxygen concentration apparatus, which is required to be reduced in size and weight, the number of parts is desired to be as few as possible. A mechanical pressure regulating valve used in a conventional oxygen concentrator is mainly constituted by a piston, a spring and a housing and its configuration requires a certain size to exhibit its features. Also, the housing that is formed of brass or aluminum may limit the reduction in weight of the apparatus. Therefore, in order to reduce the size and weight of the oxygen supply apparatus, it is desirable to omit such a mechanical pressure regulating valve. However, pressure regulation is necessary for supplying the oxygen concentrated gas to the patient stably.

Further, in the pressure swing adsorption type oxygen concentration apparatus, as the discharge pressure of the oxygen concentrated gas is reduced, the power consumption is also reduced. As a result, in the case of the portable oxygen concentration apparatus, a battery of a smaller capacity can be used and, therefore, the entire apparatus can be reduced in size and weight. However, in the mechanical pressure regulating valve, in which the regulated pressure is determined mechanically by the size of the piston and the rebounding characteristics of the spring and, therefore, which have to correspond to an optimal output with the maximum oxygen supply flow rate, the power consumption may be increased unnecessarily when the apparatus is operated with a small oxygen flow rate. Moreover, in order to adjust the pressure at the upstream of the flow rate setter to a desired value, there is a problem in that the pressure at the primary side of the pressure regulating valve or, in other words, the pressure at the output of the adsorption columns of the pressure swing adsorption type oxygen concentration apparatus has to be set higher and, as a result, the power consumption may be increased further.

Still further, when the oxygen is supplied in synchronization with the user's respiration by electromagnetic valve, which is used as the flow rate adjusting means in wherein an oxygen flow rate is controlled by an opening time of the electromagnetic valve, if the supplied flow rate is low, the opening time of the electromagnetic valve may become very short and, in particular, and depending on pressure at the upstream of the electromagnetic valve, a time for allowing a desired amount of the oxygen concentrated gas to flow may be substantially equal to a response time of the electromagnetic valve and, at this time, the electromagnetic valve may not be controlled properly.

Still further, as is apparent from the principle of the measurement of the gas concentration and flow rate by the ultrasonic type gas concentration and flow rate measuring means, when the sound velocity $V_1$ in the forward direction of the gas flow is measured and, then, the sound velocity $V_2$ in the reverse direction of the gas flow is measured, in order to cancel the gas flow velocity V to determine the concentration by the formula (3) described above, the gas flow velocity V, when $V_1$ and $V_2$ are measured, has to be constant. However, when the ultrasonic type gas concentration and flow rate measuring means is used in the respiratory synchronous oxygen concentration apparatus, wherein the flow rate of the oxygen concentrated gas flowing through the ultrasonic type gas concentration and flow rate measuring means varies very largely between the start and stop of supply of the oxygen concentrated gas, there is a problem in that a measurement error of the sound velocity C by the formula (3) may become very large and, as a result, the oxygen concentration may not be measured accurately.

The present invention has been made to solve these problems and, therefore, it is an object of the present invention to provide an oxygen concentration apparatus comprising a pressure regulating mechanism that can adjust the pressure of gas discharged from adsorption columns of a pressure swing adsorption type oxygen concentration apparatus, without using a mechanical pressure regulating valve, and that can adjust the pressure to the valve which is desirable.

Further, it is another object of the present invention to provide a respiratory synchronous type gas supply apparatus comprising ultrasonic type gas concentration and flow rate measuring means that can measure the oxygen concentration of product gas accurately.

According to the present invention, there is provided an oxygen concentration apparatus comprising:

pressure swing adsorption type oxygen concentration means including: at least one adsorption column formed of a cylinder hollow having first and second ports, an inside of the cylinder hollow is filled with an adsorbent selectively adsorbing nitrogen rather than oxygen; pressurized air supply means connected with the first port of the adsorption column and supplying pressurized air to the adsorption column; exhaust means connected with the first port of the adsorption column and allowing exhaust from the adsorption column; and switching means allowing the pressurized air supply means and the exhaust means to communicate with the first port selectively, the pressure swing adsorption type oxygen concentration means generates oxygen concentrated gas by repeating an adsorption process in which the pressurized air supply means supplies pressurized air to the adsorption column to adsorb the nitrogen from the air, and a regeneration process in which the exhaust means depressurizes the adsorption column to separate the nitrogen adsorbed by the adsorption column to regenerate the adsorbent;

a conduit communicating at its one end with the second port of the oxygen concentration means and introducing the oxygen concentrated gas generated by the oxygen concentration means from the second port into a user; and flow rate adjusting means provided in the conduit and adjusting a flow rate of the oxygen concentrated gas generated by the oxygen concentration means, the oxygen concentration apparatus further comprises:

pressure measuring means disposed between the oxygen concentration means and the flow rate adjusting means in the conduit; and control means controlling at least the switching means of the oxygen concentration means and the flow rate adjusting means, wherein the control means adjusts a cycle of the adsorption and regeneration processes of the oxygen concentration means and controls pressure at the upstream of the flow rate adjusting means by controlling the switching means based on pressure of the oxygen concentrated gas in the conduit measured by the pressure measuring means.

According to the present invention, the pressure at the upstream of the flow rate adjusting means can be adjusted without using a mechanical pressure regulating valve and the entire apparatus can be reduced in size and weight. Further, in contrast to the conventional mechanical pressure regulating valve, the adjusted pressure can be changed and the pressure can be controlled to an optimal value for each preset flow rate. In the pressure swing adsorption type oxygen concentration apparatus in which, as oxygen supply pressure is reduced, power consumption is also reduced, it is possible to reduce the power consumption. Further, in a portable oxygen concentration apparatus using a battery, the power consumption may be reduced so that usable time of the oxygen concentration apparatus can be extended and/or the apparatus may be reduced in size and weight.

Further, in the case of the respiratory synchronous oxygen supply method, in which the need of a pressure regulating valve can be eliminated and the pressure can be controlled to an optimal value for each preset flow rate, when the flow rate is low, the pressure at the upstream of on-off valve means used as the flow rate adjusting means can be reduced so that a valve opening time can become longer than a response time of the on-off valve means and, as a result, the controllability can be improved.

According to another feature of the present invention, there is provided a gas supply apparatus comprising: means for detecting a user's respiration; and a product gas flow rate on-off valve having a function to start and stop output of product gas in synchronization with the user's respiration based on a detection result, wherein the gas supply apparatus further comprises ultrasonic type gas concentration and flow rate measuring means having two ultrasonic transducers disposed in an opposed manner in a line through which the product gas flows, wherein a concentration value measured when the product gas output is stopped is determined to be a product gas concentration.

According to the present invention, as the oxygen concentration is measured while the output of the product gas flow is stopped in synchronization with the user's respiration, even in the respiratory synchronous type gas supply apparatus, the ultrasonic type gas concentration and flow rate measuring means can measure the oxygen concentration of the product gas accurately.

BRIEF DESCRIPTION OF THE DRAWINGS

FIG. 9 is a schematic diagram of an oxygen concentration apparatus used in experiment;

FIG. 10 is a schematic block diagram of a respiratory synchronization type gas supply apparatus; and FIG. 11 is a schematic block diagram of ultrasonic type gas concentration and flow rate measuring means.

BEST MODE FOR CARRYING OUT THE INVENTION

Hereinafter, preferred embodiments of the present invention will be described with reference to the drawings.

Figure 1:
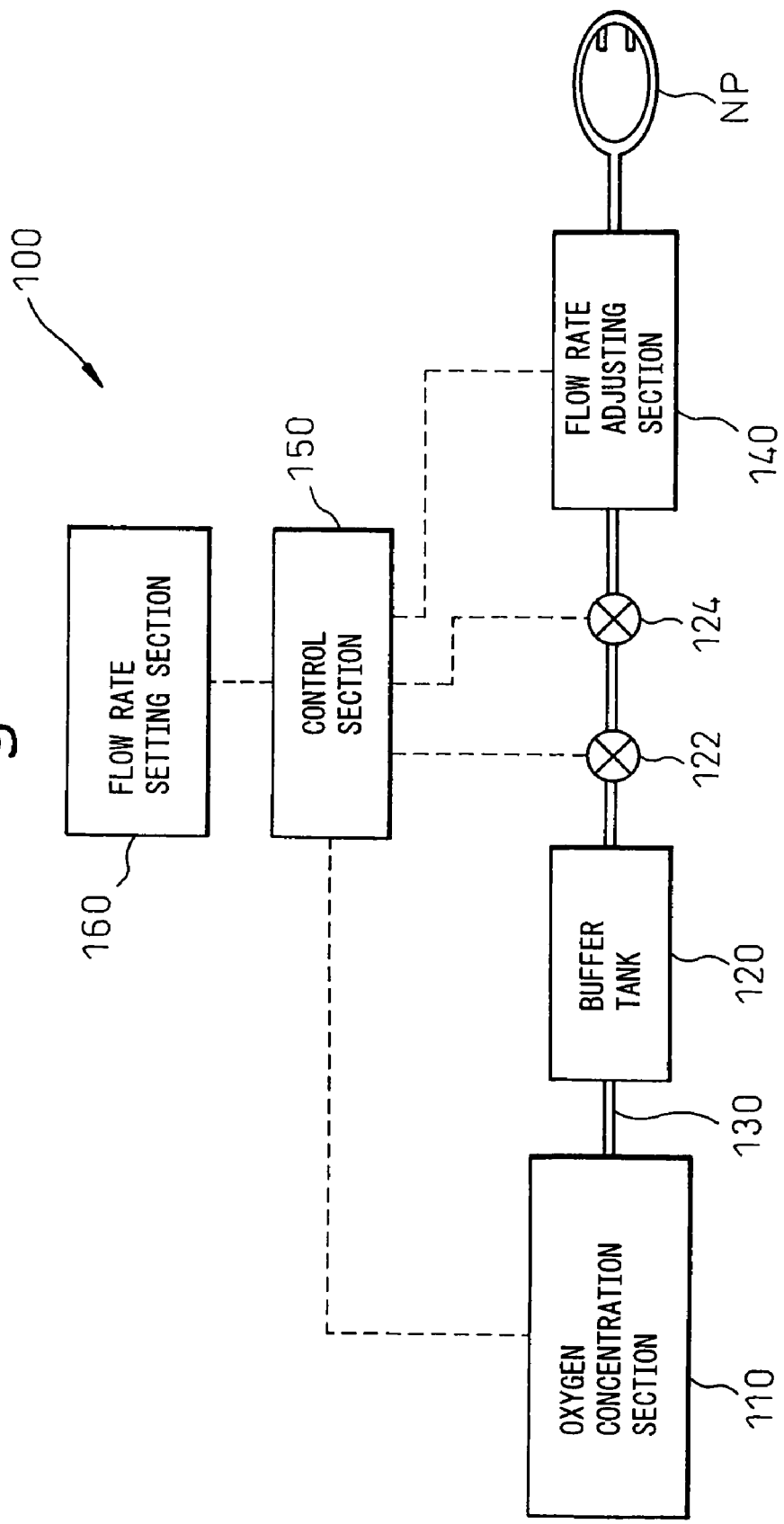
FIG. 1 is a schematic view of a preferred embodiment of the present invention.

With reference to FIG. 1, an oxygen concentration apparatus 100 according to a preferred embodiment of the present invention comprises as main components: a pressure swing adsorption type oxygen concentration section 110; a pressure sensor 122; an oxygen concentration sensor 124; a flow rate adjusting section 140; a flow rate setting section 160; and a control section 150 for controlling the effect of the oxygen concentration section 110 and the flow rate adjusting section 140, and the oxygen concentration section 110, the pressure sensor 122, the oxygen concentration sensor 124 and the flow rate adjusting section 140 are arranged along a conduit 130. A buffer tank 120 for temporarily storing oxygen concentrated gas generated in the oxygen concentration section 110 may be provided between the oxygen concentration section 110 and the flow rate adjusting section 140 along the conduit 130. As described below, in particular, when gas for respiration is supplied in synchronization with the user's respiration, the use of the buffer tank 120 allows to a reduction in the maximum generation amount of oxygen concentrated gas of the oxygen concentration section 110. The oxygen concentrated gas generated by the oxygen concentration section 110 is introduced into a patient's nostril through the buffer tank 120, the pressure sensor 122, the oxygen concentration sensor 124 and the flow rate adjusting section 140 along the conduit 130 and via a nasal cannula NP. The oxygen concentration sensor 124 may be a semiconductor sensor comprising a semiconductor, the resistance value of which varies according to the concentration of the oxygen concentrated gas. The oxygen concentration of the oxygen concentrated gas may be controlled by adjusting the number of revolutions of a compressor of the oxygen concentration section 110 based on a measurement value of the oxygen concentration sensor 124.

The oxygen concentration section 110 comprises at least: an adsorption column that is filled with an adsorbent for selectively adsorbing nitrogen; and a compressor for supplying compressed air to the adsorption column, and concentrates oxygen by alternately executing: (1) an adsorption process for introducing the compressed air into said adsorption column and adsorbing the nitrogen in a pressurized state to obtain the oxygen concentrated gas; and (2) a regeneration process for reducing internal pressure in the adsorption column to separate the nitrogen from the adsorbent to regenerate it. The oxygen concentration section 110 may be of an applied pressure swing adsorption type, a vacuum pressure swing type, or an applied and vacuum pressure swing type, depending on a range of pressure swing in the adsorption column.

The adsorption column may comprise a hollow column member formed of a material having little permeability such as metal, and the adsorbent may be a crystalline zeolite molecular sieve having selective adsorptivity to nitrogen. This zeolite is preferably a zeolite having a metallic element as a cation including, for example, sodium zeolite X, lithium zeolite X and the like.

Figure 2:
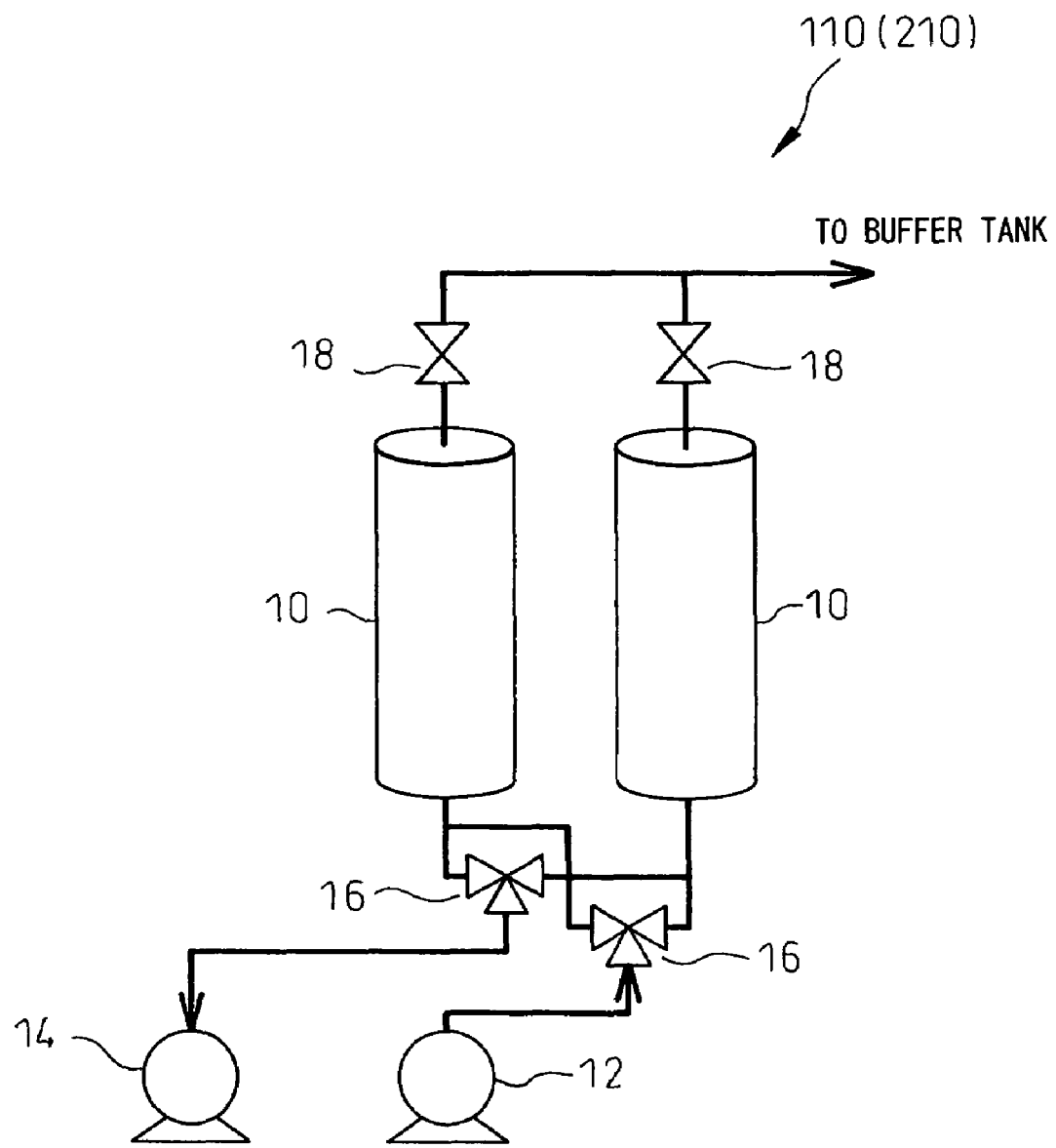
FIG. 2 is an explanatory diagram of a two-column type oxygen concentrator.

The oxygen concentration section 110 may be of multi-column type having one, two, three or more adsorption columns. FIG. 2 shows an example of a two-column type oxygen concentration section, wherein the oxygen concentration section 110 may comprise: two adsorption columns 10; a compressor 12 constituting pressurized air supplying means; a vacuum pump 14 constituting exhaust means; three-way switching valves 16 and shutoff valves 18 constituting switching means; and lines for connecting between these elements. The adsorption and regeneration processes of the adsorption columns 10 can be controlled by switching the opening and closing of the three-way switching valves 16 and the shutoff valves 18.

As apparent from FIG. 2, the adsorption columns 10 have first ports communicating with the compressor 12 as the pressurized air supplying means and the vacuum pump 14 as the exhaust means and second ports communicating with the conduit 130. Here, the compressor 12 may be used also as the exhaust means in a combined manner. Further, the exhaust means may simply be a muffler for discharging nitrogen gas into atmosphere.

Figure 3:
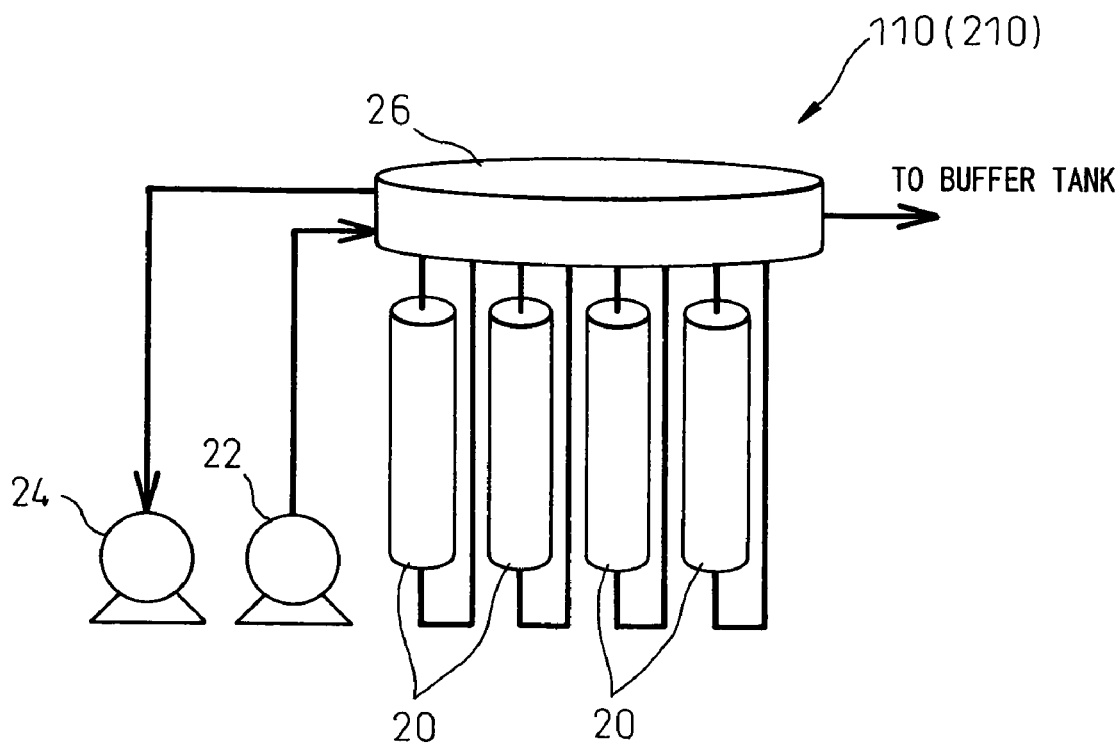
FIG. 3 is an explanatory diagram of a multi-column type oxygen concentrator.

FIG. 3 shows an example of a multi-column type oxygen concentration section, wherein the oxygen concentration section 110 comprises: a plurality of (four in the example of FIG. 3) adsorption columns 20, a compressor 22 constituting pressurization means; a vacuum pump 24 constituting exhaust means; and a rotary valve 26 communicating with each adsorption column 20. In this example, the rotary valve 26 constitutes switching means so that the adsorption columns 22 can be switched between the adsorption and regeneration processes by rotation of the rotary valve 26.

As is apparent from FIG. 3, the adsorption columns 20 also have first ports communicating with the compressor 22 as the pressurized air supplying means and the vacuum pump 24 as the exhaust means and second ports communicating with the conduit 130. Here, the compressor 22 may be used also as the exhaust means in a combined manner. Further, the exhaust means may simply be a muffler for discharging the nitrogen gas into the atmosphere.

The patient or user can set the output flow rate from the nasal cannula NP by the flow rate setting section 160. By way of example, the flow rate setting section 160 may comprise a rotary switch (not shown) or a potentiometer (not shown) the setting position of which corresponds to the flow rate, and the flow rate setting section 160 specifies the flow rate of the oxygen concentrated gas output from the nasal cannula NP to the control section 150. The control section 150 reads the flow rate set by the flow rate setter 160. As described below, the control section 150 controls the oxygen concentration section 110 and the flow rate adjusting section 140 so that the flow rate set by the flow rate setter 160 can be output from the nasal cannula NP.

Figure 4:
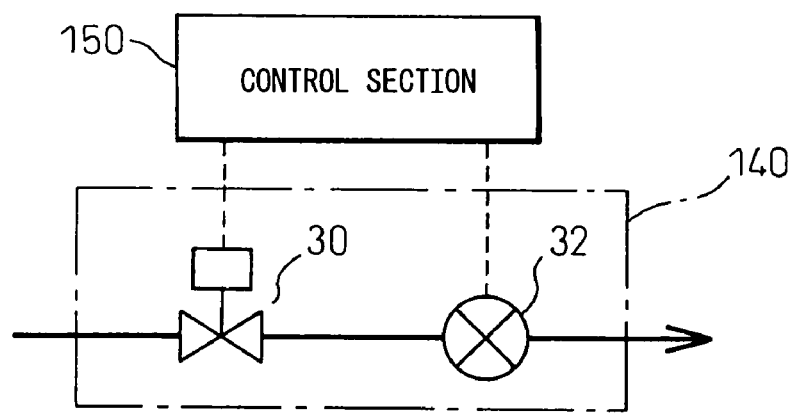
FIG. 4 is a diagram showing an example of a flow rate adjusting section (of a continuous type)

With reference to FIG. 4, in an embodiment of the present invention, the flow rate adjusting section 140 comprises: a throttle valve 30; and a flow rate sensor disposed downstream of the throttle valve 32. The throttle valve 30 comprises: a valve element that can be movable between an opened position, in which the valve is opened completely, and a closed position, in which the valve is closed completely; a spring that urges said valve element toward said closed position; and a solenoid connected with the control section 150, and the throttle valve 30 may act as a solenoid type proportional valve that can infinitely position said valve element between said opened and closed positions in proportion to a control current value supplied from the control section 150 to said solenoid. The flow rate sensor 32 may comprise a hot wire type flowmeter, a differential pressure type flowmeter, a supersonic type flowmeter, a gear type flowmeter and the like connected with the control section 150.

The control section 150 changes the current value supplied to said solenoid based on the flow rate measured by the flow rate sensor 32 to control the degree of opening of the throttle valve 30 so that the oxygen concentrated gas of the flow rate set by the flow rate setter 160 is output continuously from the nasal cannula NP. Here, the flow rate sensor 32 does not always have to be provided downstream of the throttle valve 30 but it may be disposed between the oxygen concentration section 110 and the throttle valve 30. The essential thing is that the flow rate sensor 32 is disposed at an appropriate position along the conduit 130 where the flow rate of the oxygen concentrated gas output from the nasal cannula NP can be measured accurately.

While the oxygen concentrated gas generated by the oxygen concentration section 110 is adjusted to a specific constant flow rate by the flow rate adjusting section 140 and supplied to the patient, the pressure sensor 122 measures pressure in the conduit 130. The measurement result is sent to the control section 150 and, based on the measurement result, the control section 150 adjusts a cycle of the adsorption and regeneration processes of the adsorption columns 20 of the oxygen concentration section 110 to control the pressure in the conduit. More specifically, if the cycle of the adsorption and regeneration processes becomes faster, pressure of the oxygen concentrated gas discharged from the pressure swing adsorption type oxygen concentration section 110 is reduced and, if the cycle becomes slower, the pressure is increased. Therefore, the pressure in the conduit can be controlled to a specific pressure by accelerating the cycle of the adsorption and regeneration processes when the pressure in the conduit is increased and decelerating the cycle when the pressure is reduced.

In the case of pressure swing adsorption type oxygen concentration means of a multi-column type, in which the adsorption columns 20 are connected with the pressurization and depressurization means 22, 24 via the rotary valve 26, the control section 150 can control the pressure in the conduit by adjusting rotation speed of the rotary valve based on pressure information measured by the pressure sensor 122.

The pressure information measured by the pressure sensor 122 and, then, sent to the control section 150 is preferably subject to a moving average process in the control section 150. The cycle of the adsorption and regeneration processes of the oxygen concentration section 110 may be adjusted so that the pressure value after the moving average process is a target pressure value. In the pressure swing adsorption type oxygen concentration means, in which the pressure of the oxygen concentrated gas discharged from the adsorption columns fluctuates according to the cycle of the adsorption and regeneration processes, the pressure in the conduit can be controlled more stably by executing the moving average process. The moving average process can remove the fluctuation components. When the buffer tank 120 is small, the pressure swing is significant and makes it difficult to control the pressure stably, but the stable control can be possible by executing the moving average process to remove the fluctuation components. It eliminates the need to increase the size of the buffer 120 to suppress the pressure swing and it is advantageous in terms of miniaturization.

Therefore, a load on the pressure swing adsorption type oxygen concentration section 110 can be reduced by selecting an appropriate minimum pressure for each flow rate set value. Here, once the oxygen concentration and the flow rate of the oxygen concentrated gas supplied by the oxygen concentration section 110 are determined, the output of the pressurization and depressurization means is also determined accordingly. The output value can be obtained in advance and the respective outputs of the pressurization and depressurization means can be controlled by the control section 150 according to the setting of the flow rate setting section 160. As the flow rate of the oxygen concentrated gas is increased, or as the concentration of the oxygen concentrated gas is increased, the output of the pressurization and depressurization means is increased.

Figure 5:
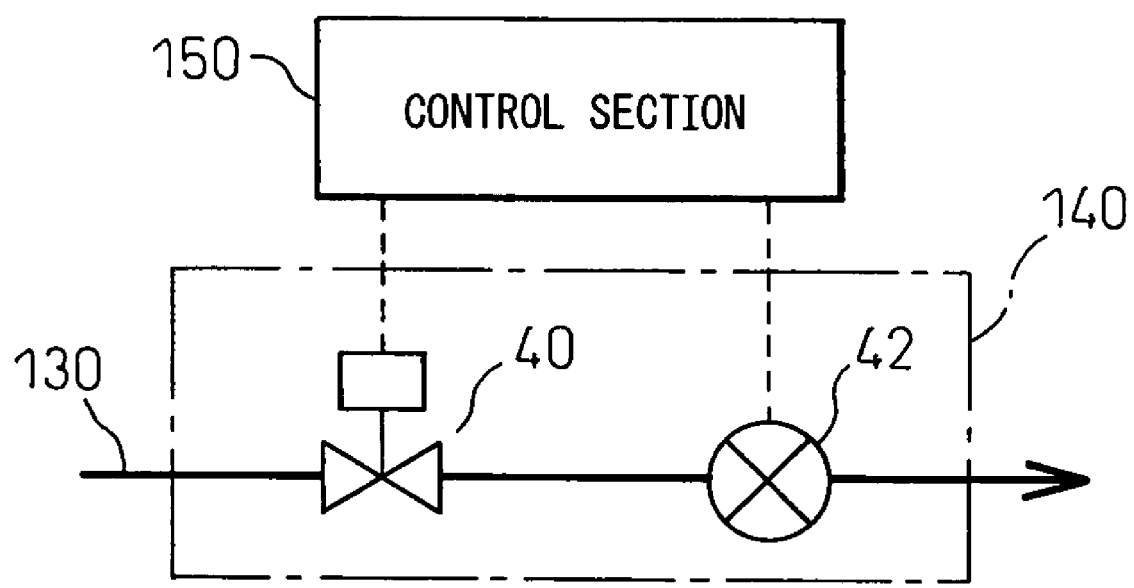
FIG. 5 is a diagram showing an example of a flow rate adjusting section (of a respiratory synchronization type)

Next, with reference to FIG. 5, another example of a flow rate adjusting section 140 will be described. In the embodiment of FIG. 5, a flow rate control section 150 comprises an on-off valve 40 and a pressure sensor 42 that is disposed downstream of the on-off valve 40 as means for detecting the patient's respiratory phase, and supplies oxygen concentrated gas only in an inspiratory phase or in a portion of an inspiratory phase. The =on-off valve 40 comprises: a valve element that can be movable selectively between an opened position, in which the valve is opened completely, and a closed position, in which the valve is closed completely; a spring that urges said valve element toward said closed position; and a solenoid connected with the control section 150, and the on-off valve 40 may act as a solenoid type on-off valve in which said valve element is moved to said opened position when the control section 150 supplies current to said solenoid. The pressure sensor 42 may be a semiconductor type pressure transducer and the like connected with the control section 150. As expiratory air flows into the cannula to increase its internal pressure when the user is in an expiratory phase and air in the cannula flows out from the cannula when the user is in an inspiratory phase, the start of the inspiratory phase can be detected by reading this change. The point where the pressure in the conduit 130 is changed from positive pressure to negative pressure can be determined as a starting point of the inspiratory phase based on the output of the pressure sensor 42 and the oxygen concentrated gas can be supplied only in the inspiratory phase or in a portion of the inspiratory phase so that the patient's utilization efficiency of the oxygen concentrated gas can be increased.

Hereinafter, an example of a control in such configuration will be exemplified. In a time range in which a flow rate per minute, which is calculated based on the flow rate set by the flow rate setting section 160 and the start of the inspiratory phase detected by the pressure sensor 42 as the respiratory phase detection means, is constant, the on-off valve 40 is opened for a specific time period in synchronization with the start of the inspiratory phase. Here, the flow rate per minute can be given by the following formula (8):

$$Q = n \times q \quad (8)$$

where,
Q: a flow rate per minute ($cm^3$/min),
n: a respiration rate (1/min), and
q: a flow rate supplied while the electromagnetic valve is opened once ($cm^3$).

Therefore, in order to make the flow rate per minute Q constant, if the respiratory rate per minute n is increased, the flow rate supplied while the electromagnetic valve is opened once q may be reduced and, if the respiratory rate per minute n is reduced, the flow rate supplied while the electromagnetic valve is opened once q may be increased. Here, the flow rate per minute Q can be given by the flow rate setting section 160 as a preset flow rate and the respiratory per minute n can be calculated from the several previous time ranges of the inspiratory phase detected by the pressure sensor 42. Therefore, the flow rate supplied while the electromagnetic valve is opened once q can be given by the following formula (9):

$$q = Q'/n \quad (9)$$

where,

Q': a preset flow rate ($cm^3$/min).

On the other hand, the opening time range of the on-off valve 40, from which the flow rate supplied while the electromagnetic valve is opened once q is calculated, depends on a pressure difference between the upstream and downstream sides of the on-off valve 40. Here, the downstream of the on-off valve 40 is connected with the nasal cannula NP and the pressure at the downstream side of the on-off valve 40 can be assumed to be approximately atmospheric pressure. Therefore, the flow rate q mainly depends on the pressure at the upstream side of the on-off valve 40. If the pressure at the upstream side of the on-off valve 40 or, in other words, the pressure at the exit of the buffer tank 120 is controlled to be constant, the opening time range to give a desired flow rate q can be calculated automatically once the preset flow rate Q' and the respiratory rate per minute n are determined.

Here, it is to be noted that, as the pressure at the upstream side of the on-off valve 40 is increased, the opening time range of the on-off valve 40 has to be reduced accordingly and, when the pressure at the upstream side of the on-off valve 40 becomes too high, controllability of the on-off valve 40 may be degraded. In such cases, the pressure to be controlled is set to be a reduced value according to each preset flow rate Q'.

Further, in this embodiment, in particular, an appropriate capacity of the buffer tank 120 can be selected based on the maximum value of the flow rate q supplied while the electromagnetic valve is opened once.

Next, with reference to FIG. 6, a further embodiment of the present invention will be described.

Figure 6:
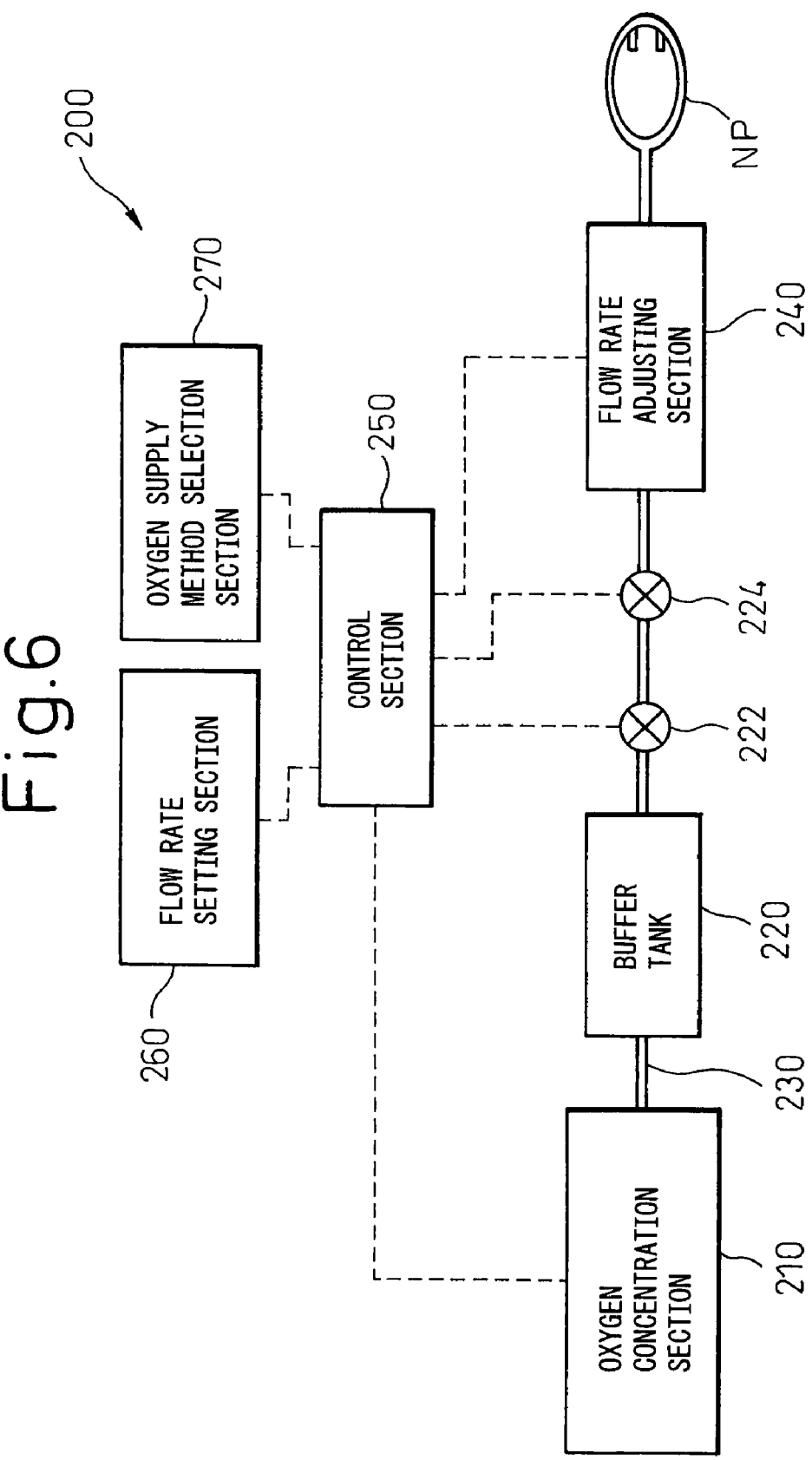
FIG. 6 is a schematic view of another embodiment of the present invention.

An oxygen concentration apparatus 200 according to the embodiment shown in FIG. 6 comprises, as main components: a pressure swing adsorption type oxygen concentration section 210; a pressure sensor 222; an oxygen concentration sensor 224; a flow rate adjusting section 240; a flow rate setting section 260; an oxygen supply method selection section 270; an oxygen concentration section 210; and a control section 250 for controlling the effect of the flow rate adjusting section 250, and the oxygen concentration section 210, the pressure sensor 222, the oxygen concentration sensor 224, and the flow rate adjusting section 240 are arranged along a conduit 230. A buffer tank 220 for temporarily storing oxygen concentrated gas generated in the oxygen concentration section 210 may be provided between the oxygen concentration section 210 and the flow rate adjusting section 240 along the conduit 230.

This embodiment is configured substantially similarly to that of FIG. 1, except that this embodiment comprises the oxygen supply method selection section 270 for switching the oxygen supply method between the continuous supply mode and the synchronous supply mode described above. Therefore, in the following, only the difference from the embodiment of FIG. 1 will be described.

The oxygen supply method selection section 270 can comprise a switch that has at least two positions corresponding to the synchronous mode and the continuous mode described above and that is connected with the control section 250 so that the patient or user can select the supply method of the oxygen concentrated gas between the synchronous mode, in which the oxygen concentrated gas is supplied intermittently in synchronization with the user's respiration, and the continuous mode, in which the oxygen concentrated gas is supplied continuously.

Figure 7:
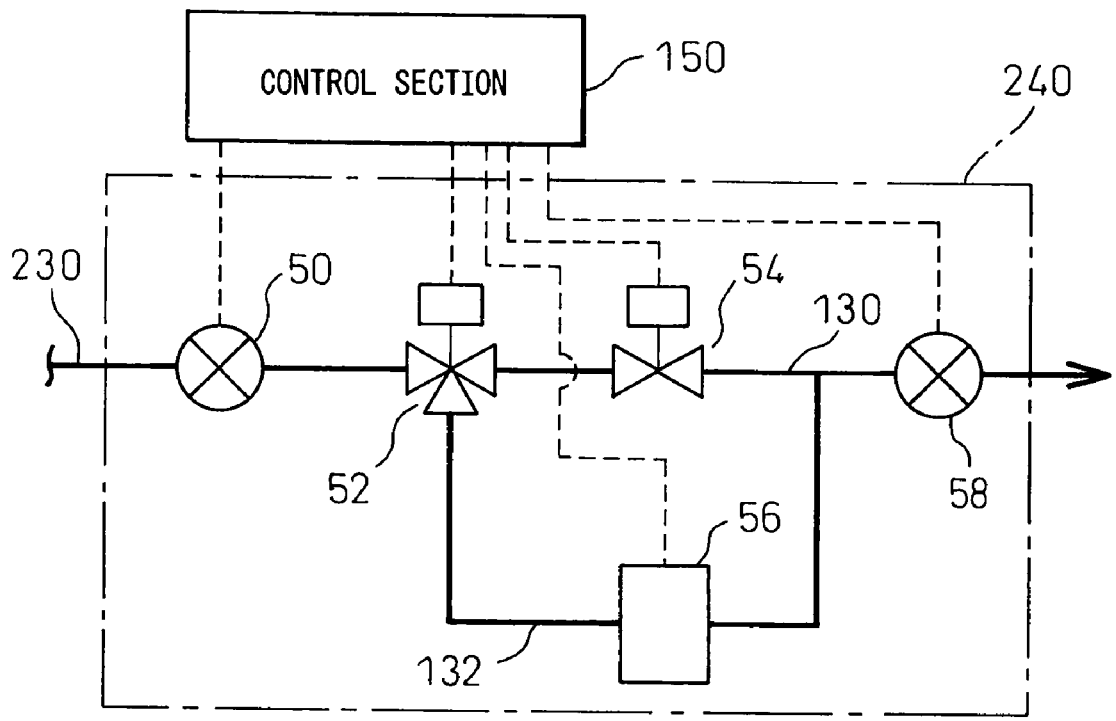
FIG. 7 is a diagram showing an example of a flow rate adjusting section (that is switched between the respiratory synchronization/continuous types)

On the other hand, as shown in FIG. 7, by way of example, the flow rate adjusting section 240 comprises: a flow rate sensor 50; a three-way switching valve 52; an on-off valve 54; a pressure sensor 58; a branched line 132 that is branched from the conduit 230 via the three-way switching valve 52 and that joins with the conduit 230 between the on-off valve 54 and the pressure sensor 58; and a variable orifice 56 that is provided in the branched line 132. In the variable orifice 56, in which a plurality of orifices, each of which has a hole diameter that can pass a specific flow rate under an upstream pressure controlled to a constant value, are arranged as a concentric disc, one orifice can be disposed concentrically with the conduit by rotating the disc to restrict the flow of the oxygen concentrated gas so that the oxygen concentrated gas of a desired flow rate can be supplied to the patient continuously.

When the mode to supply in synchronization with the respiration is selected, the on-off valve 54 is opened and closed at the opening time range calculated based on information from the flow rate setting section 260 and information from the pressure sensor 58 constituting respiratory phase detection means. When the mode to supply continuously is selected, the orifice 33 or the throttle valve means 33 can be configured to supply a flow rate according to the flow rate setting section 260. It allows the patient to select the preferred one from the respiratory synchronous intermittent oxygen supply and the continuous oxygen supply.

Figure 8:
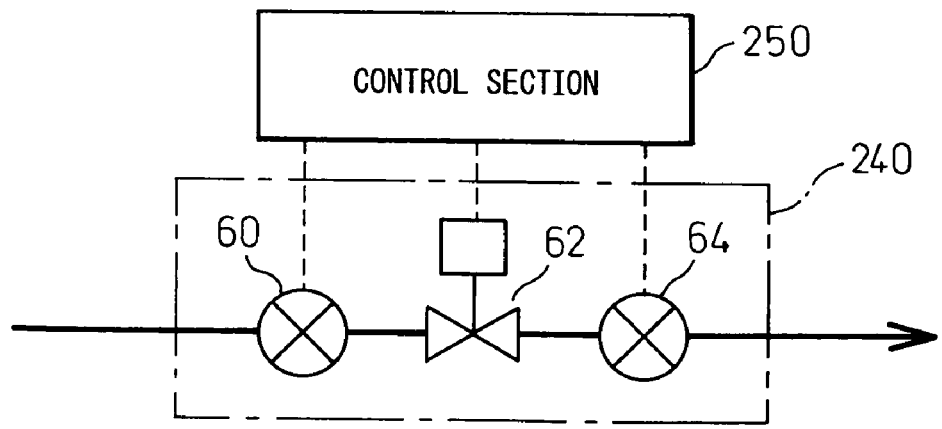
FIG. 8 is a diagram showing an example of a flow rate adjusting section (that is switched between the respiratory synchronization/continuous types)

FIG. 8 shows a variation of the embodiment of FIG. 7. In the embodiment of FIG. 8, the flow rate adjusting section 240 comprises: a throttle valve 62; a flow rate sensor 60; and a pressure sensor 64 as respiratory phase detection means. When the synchronous mode to supply in synchronization with the respiration is selected, the throttle valve 62 is controlled between the full-opened and full-closed states based on information from the flow rate setter 160 and information from the pressure sensor 64 to supply oxygen in a respiratory synchronous intermittent manner. When the mode to supply continuously is selected, the throttle valve 62 can be controlled based on information from the flow rate setting section 260 and the flow rate sensor 60 to supply a specific flow rate.

FIG. 9 shows an apparatus used for experiment. In FIG. 9, the oxygen concentration apparatus 100 comprises: a pressure swing type oxygen concentration section 310; a buffer tank 320; a pressure sensor 322 for measuring pressure in the buffer tank 320; a flow rate adjusting section 340; a flow rate setting section 360; an oxygen supply method selection section 370; and a control section 350 for controlling the effect of the oxygen concentration section 310 and the flow rate adjusting section 340. The oxygen concentration section 310 is a four-column applied and vacuum pressure swing type oxygen concentrator that comprises: four adsorption columns 312; a compressor 314 that can increase and reduce pressure; and a rotary valve 316 and that generates oxygen concentrated gas at an oxygen concentration of 90% at a rate of 1000 cm$^3$/min.

Further, the flow rate adjusting section 340 comprises: an ultrasonic type flow rate sensor 342; a throttle valve 344; and a pressure sensor 346 constituting respiratory phase detection means. The throttle valve 344 comprises a solenoid type proportional valve having a maximum orifice diameter of ϕ1.7 mm. The pressure sensor 346 has a pressure measuring range of ±75 Pa and the point where the pressure measured by the pressure sensor 346 is changed from positive pressure to negative pressure is determined as a starting point of the inspiratory phase. Further, the output of the pressure sensor 322 undergoes a moving average process of 20 seconds and the number of revolutions of the rotary valve 316 is adjusted so that the moving average value is 20 kPa.

The oxygen supply method was set to the respiratory synchronous mode by the oxygen supply method selection section 370 and the flow rate was preset to 3000 cm$^3$/min by the flow rate setting section 360. Based on the idea that the oxygen supplied in expiratory time is wasted and, therefore, the oxygen should be supplied only in inspiratory time and, further, based on the fact that the ratio between the inspiration and expiration of human breathing is generally 1:2, the substantial supplied flow rate was set to 1000 cm$^3$/min. Here, the ratio between the inspiration and expiration of human breathing is not always limited to 1:2.

As the buffer tank 320 had a capacity of 250 cm$^3$ and the throttle valve means 344 had an orifice diameter of ϕ1.7 mm, the buffer tank 320 might have an average pressure of 20 kPa to supply the amount required for the preset flow rate of 3000 cm$^3$/min (the substantial flow rate of 1000 cm$^3$/min) in the mode to supply in synchronization with the respiration. For example, if the flow rate is preset to 5000 cm$^3$/min (the substantial flow rate of 1670 cm$^3$/min), the average pressure of the buffer tank 320 of 40 kPa is required. In this case, a regression curve that had been derived from data measured in experiment in advance was utilized to calculate an appropriate time range while the valve was opened once from the preset flow rate and the respiratory rate.

A negative pressure pump and an electromagnetic valve that was opened and closed repeatedly at specific intervals periodically generated negative pressure at the end of the nasal cannula NP as artificial respiration. In synchronization with the start of the inspiratory phase of the artificial respiration detected by the pressure sensor 346, the control section 350 opened and closed the throttle valve 344 between the full-opened and full-closed states to supply oxygen. The throttle valve 344 was opened and closed in a time range that allowed the flow rate per minute that was calculated from the preset flow rate of 3000 cm$^3$/min and the respiratory rate/min to be constant, or, in this case, to be 1000 cm$^3$/min. At this time, the actually measured flow rate per minute supplied to the user was about 1000 cm$^3$/min.

On the other hand, the oxygen supply method was set to the continuous supply mode, in which the oxygen concentrated gas was supplied continuously, by the oxygen supply method selection section 370. At this time, the throttle valve means 344 was controlled so that the flow rate value measured by the flow rate sensor 342 was the preset flow rate of 3000 cm$^3$/min. Here, when the oxygen was supplied continuously, the oxygen concentrated gas was supplied at a flow rate that had been set by the flow rate setting section 360 and, therefore, the compressor 314 was controlled to generate an output flow rate of 3000 cm$^3$/min. As a result, the actually measured flow rate that was supplied continuously was 3000 cm$^3$/min.

FIG. 10 shows a still further embodiment of the present invention.

In FIG. 10, an oxygen concentration apparatus 400 comprises: oxygen concentration means 406 that separates oxygen from air; a compressor 404 that supplies the air as source gas to the oxygen concentration means 406; a filter 402 that removes dust included in the air supplied to the oxygen concentration means 406; gas pressure adjusting means 408 that adjusts pressure of the oxygen concentrated gas as product gas; ultrasonic type gas concentration and flow rate measuring means 410; a product gas flow path on-off valve 412; respiration detection means 414 that detects the user's respiration; and, further, a main controller 416 that is connected electrically for controlling these components.

FIG. 11 shows a schematic configuration of the ultrasonic type gas concentration and flow rate measuring means 410.

Two ultrasonic transducers 420 that can transmit and receive ultrasonic waves are disposed at both ends of a line 422 that constitutes a test line having a circular cross-section and extending linearly. The ultrasonic transducers 420 are arranged in an opposed manner in the line 422 through which product gas flows and, in this embodiment, an ultrasonic transducer having a center frequency of 40 kHz is adopted.

Two temperature sensors 424 are disposed in the vicinity of ports of the product gas so as not to disturb the gas flow on the ultrasonic propagation path. The two temperature sensors 424 are disposed at the ports of the line 422 so that an average temperature of the product gas flowing through the line 422 can be measured. If temperature variation of the product gas is not large, only one temperature sensor 424 may suffice.

The respiration detection means 414 preferably comprises a micro differential pressure sensor. In order to detect the respiration of the user, the main controller 416 detects the start of the inspiratory phase based on pressure swing output from the micro differential pressure sensor.

Hereinafter, an effect of the oxygen concentration apparatus 400 in this embodiment will be described.

When the respiration of the user is not detected, the product gas flow path on-off valve 412 is closed. In the oxygen concentration apparatus 400, till the inspiration of the user is detected, in preparation for supplying necessary product gas to the user, the compressor 404 pressurizes the source gas and supplies it to the oxygen concentration means 406 and the oxygen concentration means 406 generates high concentration oxygen concentrated gas as the product gas. The gas pressure adjusting means 408 can maintain the pressure of the product gas at a specific level at the upstream of the gas flow path on-off valve 412.

When the user starts respiration and the supply of the product gas is started, the respiration detection means 414 detects the start of the inspiratory phase of the user. Once the start of the inspiratory phase is detected, the main controller 416 calculates a valve opening time required to supply a preset amount of the product gas to the user based on information about current pressure of the product gas adjusted by the gas pressure adjusting means 408 and opens the gas flow path on-off valve 412 during the valve opening time. Then, the gas flow path on-off valve 412 is closed and the above process is repeated.

The oxygen concentration apparatus 400 uses the ultrasonic type gas concentration and flow rate measuring means 410 to determine whether the product gas exceeds the preset oxygen concentration or not. The ultrasonic type gas concentration and flow rate measuring means 410 can detect an accurate oxygen concentration when the product gas flow is stopped in the conduit and, therefore, the main controller 416 sends a signal to start measurement to the ultrasonic type gas concentration and flow rate measuring means 410 while the product gas flow path on-off valve 412 is closed.

Then, a microcomputer 430 in the ultrasonic type gas concentration and flow rate measuring means 410 sends a signal to transmit ultrasonic waves to a driver 426 so that one of the ultrasonic transducers 420 selected via a transmit/receive switch 434 can transmit the ultrasonic waves. The other of the ultrasonic transducers 420 receives the transmitted ultrasonic waves and the received ultrasonic waves is received as an electric signal by a receiver 428 via the transmit/receive switch 434 and, then, sent to the microcomputer 430. The microcomputer 420 calculates the sound velocity in the product gas from the time to transmit and receive the signal.

Then, the microcomputer 420 switches the direction of transmission/reception of the ultrasonic waves via the transmit/receive switch 434 and calculates sound velocity in the reverse direction by the method described above. This calculation of the sound velocity is performed repeatedly till the inspiration of the user is detected and the gas flow path on-off valve 412 is opened. A plurality of calculation results are summed and averaged so that a measurement error of the sound velocity can be reduced.

Simultaneously with the transmission/reception of the ultrasonic waves mentioned above, the microcomputer 430 also detects temperature of the product gas via the temperature sensor 424. When the inspiration of the user is detected, the main controller 416 sends a signal to stop the measurement to the ultrasonic type gas concentration and flow rate measuring means 410. Upon receiving this stop signal, the microcomputer 430 calculates the oxygen concentration of the product gas from the sound velocity and the product gas temperature that are detected hitherto based on the formula (4) mentioned above. More specifically, for example, the oxygen concentration can be calculated by using the methods shown in Patent Documents 4 and 5 mentioned above. The calculated value of the oxygen concentration is sent back from the microcomputer 430 to the main controller 416.

Though this embodiment is configured so that the main controller 416 determines that the output of the product gas is stopped, the ultrasonic type gas concentration and flow rate measuring means 410 can measure not only the gas concentration but also the gas flow rate and, therefore, the ultrasonic type gas concentration and flow rate measuring means 410 can also determine that the product gas flow is stopped. Thus, the ultrasonic type gas concentration and flow rate measuring means 410 may repeat transmission and reception of the ultrasonic waves continuously and detect the gas flow rate each time and, if only the gas flow rate can be determined to be zero, the oxygen concentration of the product gas may be calculated and the calculated oxygen concentration may be sent to the main controller 416.

What is claimed is:

1. An oxygen concentration apparatus comprising:
pressure swing adsorption type oxygen concentration means including: at least one adsorption column formed of a cylinder hollow having first and second ports, an inside of said cylinder hollow is filled with an adsorbent selectively adsorbing nitrogen rather than oxygen;
pressurized air supply means connected with the first port of said adsorption column and supplying pressurized air to said adsorption column; exhaust means connected with the first port of said adsorption column and allowing exhaust from said adsorption column; and switching means allowing said pressurized air supply means and said exhaust means to communicate with said first port selectively, said pressure swing adsorption type oxygen concentration means generates oxygen concentrated gas by repeating an adsorption process in which said pressurized air supply means supplies pressurized air to said adsorption column to adsorb the nitrogen from said air, and a regeneration process in which said exhaust means depressurizes said adsorption column to separate the nitrogen adsorbed by said adsorption column to regenerate said adsorbent;

a conduit communicating at its one end with the second port of said oxygen concentration means and introducing the oxygen concentrated gas generated by said oxygen concentration means from said second port into a user; and flow rate adjusting means provided in said conduit and adjusting a flow rate of the oxygen concentrated gas generated by said oxygen concentration means, said oxygen concentration apparatus further comprises:

pressure measuring means disposed between said oxygen concentration means and said flow rate adjusting means in said conduit; and control means controlling at least the switching means of said oxygen concentration means and said flow rate adjusting means, wherein said control means adjusts a cycle of the adsorption and regeneration processes of said oxygen concentration means and controls pressure at the upstream of said flow rate adjusting means by controlling said switching means based on pressure of said oxygen concentrated gas in said conduit measured by said pressure measuring means.

2. An oxygen concentration apparatus according to claim 1, wherein said oxygen concentration means has a multi adsorption columns, and said switching means having a rotary valve allowing each of said multi adsorption columns to communicate with said pressurized air supply means and said exhaust means selectively, said control means controlling the number of revolutions of said rotary valve.

3. An oxygen concentration apparatus according to claim 1, further comprising flow rate setting means for setting a flow rate of the oxygen concentrated gas to be supplied to the user, wherein said control means controls said switching means to adjust a cycle of the adsorption and regeneration processes so that the flow rate of the oxygen concentrated gas set by said flow rate setting means can be obtained.

4. An oxygen concentration apparatus according to claim 3, wherein said control means executes a moving average process of pressure in said conduit measured by said pressure measuring means in terms of time and controls said switching means to adjust the cycle of the adsorption and regeneration processes of the oxygen concentration means so that the pressure after the moving average process is a target pressure value.

5. An oxygen concentration apparatus according to claim 3, wherein said flow rate adjusting means having an on-off valve disposed in said conduit; and respiratory phase detection means disposed downstream of said on-off valve in said conduit and detecting a respiratory phase of the user, wherein said control means calculates a valve opening time of said on-off valve based on the flow rate of the oxygen concentrated gas set by said flow rate setting means and information about a respiratory phase detected by said respiratory phase detection means to open said on-off valve during said valve opening time from a start of an inspiratory phase detected by said respiratory phase detection means.

6. An oxygen concentration apparatus according to claim 3, wherein said flow rate adjusting means further includes a variable orifice having a plurality of orifices of different diameters and disposed in said conduit, wherein said control means selects one orifice of said plurality of orifices so that said oxygen concentrated gas can pass through said variable orifice at a flow rate set by said flow rate setting means.

7. An oxygen concentration apparatus according to claim 3, wherein said flow rate adjusting means includes a proportional valve disposed in said conduit; and flow rate measuring means disposed at the upstream or downstream of said on-off valve in said conduit, wherein said control means controls a degree of opening of said proportional valve so that a measured value by said flow rate measuring means can coincide with a flow rate of the oxygen concentrated gas set by said flow rate setting means.

8. An oxygen concentration apparatus according to claim 5, further comprising oxygen supply method selection means for selecting between a continuous mode to supply the oxygen concentrated gas to the user continuously and a synchronous mode to supply in synchronization with the user's respiration, wherein said flow rate adjusting means further including:

a three-way valve disposed upstream of said on-off valve in said conduit;

a branched line branched from said conduit via said three-way valve and joining with said conduit at the downstream of said on-off valve; and a variable orifice disposed in said branched line and having a plurality of orifices of different diameters, wherein, when said synchronous mode is selected, said control means shuts off said branched line from said conduit and calculates the valve opening time of said on-off valve based on the flow rate of the oxygen concentrated gas set by said flow rate setting means and the information about the respiratory phase detected by said respiratory phase detection means to open said on-off valve during said valve opening time from the start of the inspiratory phase detected by said respiratory phase detection means, and, when said continuous mode is selected, said control means connects said branched line with said conduit and selects one orifice of said plurality of orifices so that said oxygen concentrated gas can pass through said variable orifice at a flow rate set by said flow rate setting means.

9. An oxygen concentration apparatus according to claim 5, further comprising oxygen supply method selection means for selecting between a continuous mode to supply the oxygen concentrated gas to the user continuously and a synchronous mode to supply the oxygen-concentrated gas in synchronization with the user's respiration, wherein said flow rate measuring means is disposed downstream of said on-off valve in the conduit, and said flow rate adjusting means further including:

a three-way valve disposed upstream of said on-off valve in said conduit;

a branched line branched from said conduit via said three-way valve and flowing into said conduit at the downstream of said valve and at the upstream of said flow rate measuring means; and a proportional valve disposed in said branched line wherein when said synchronous mode is selected, said control means shuts off said branched line from said conduit and calculates the valve opening time of said on-off valve based on the flow rate of the oxygen concentrated gas set by said flow rate setting means and the information about the respiratory phase detected by said respiratory phase detection means to open said on-off valve during said valve opening time from the start of the inspiratory phase detected by said respiratory phase detection means, when said continuous mode is selected, said control means connects said branched line with said conduit and controls a degree of opening of said proportional valve so that a measured value by said flow rate measuring means can coincide with a flow rate of the oxygen concentrated gas set by said flow rate setting means.

10. An oxygen concentration apparatus according to claim 5, further comprising oxygen supply method selection means for selecting between a continuous mode to supply the oxygen concentrated gas to the user continuously and a synchronous mode to supply the oxygen-concentrated gas in synchronization with the user's respiration, and wherein said flow rate adjusting means further including:
a proportional valve disposed in said conduit; and
respiratory phase detection means disposed downstream of said proportional valve in said conduit and detecting a respiratory phase of the user,
wherein when said synchronous mode is selected, said control means calculates the valve opening time of said on-off valve based on the flow rate of the oxygen concentrated gas set by said flow rate setting means and the information about the respiratory phase detected by said respiratory phase detection means to open said on-off valve during said valve opening time from the start of the inspiratory phase detected by said respiratory phase detection means, and, when said continuous mode is selected, said control means controls a degree of opening of said proportional valve so that a value measured by said flow rate measuring means can coincide with a flow rate of the oxygen concentrated gas set by said flow rate setting means.

11. An oxygen concentration apparatus according to claim 1, further comprising oxygen concentration measuring means disposed at the upstream or downstream of said flow rate adjusting means in said conduit, wherein said control means controls said pressurized air supply means so that an oxygen concentration measured by said oxygen concentration measuring means can be a desired oxygen concentration.

12. An oxygen concentration apparatus according to claim 11, wherein said oxygen concentration measuring means includes an ultrasonic type gas concentration and flow rate measuring apparatus having: a test line that extending linearly; and two ultrasonic transducers disposed in an opposed manner in said test line, said ultrasonic type gas concentration and flow rate measuring apparatus measuring an oxygen concentration and a flow rate of the oxygen concentrated gas by ultrasonic waves, wherein an oxygen concentration is measured while the oxygen concentrated gas is immobile in said test line.

13. An oxygen concentration apparatus according to claim 12, wherein it is determined that the oxygen concentrated gas is immobile based on a flow rate measured by said ultrasonic type gas concentration and flow rate measuring apparatus.

14. An oxygen concentration apparatus according to claim 5, further comprising ultrasonic type gas concentration and flow rate measuring means having two ultrasonic transducers disposed in an opposed manner in the line through which the product gas flows, wherein a concentration value measured when said product gas output is stopped is determined to be a product gas concentration.

15. An oxygen concentrating apparatus according to claim 14, wherein it is determined that the product gas output is stopped based on a flow rate output value measured by the ultrasonic-type gas-concentration and flow rate measuring apparatus itself.

16. An oxygen concentrating apparatus according to claim 14, wherein it is determined that the product gas output is stopped based on information from the means for controlling the start and stop of the output of the product gas.

17. An oxygen concentration apparatus according to claim 14, wherein said ultrasonic type gas concentration and flow rate measuring means is disposed upstream of said product gas flow path on-off valve.

* * * * *